(12) United States Patent
Potter (10) Patent No.: US 8,373,206 B2
(45) Date of Patent: Feb. 12, 2013

(54) BIOSENSOR APPARATUSES AND METHODS THEREOF

(75) Inventor: Michael Potter, Churchville, NY (US)

(73) Assignee: NTH Tech Corporation, Churchville, NY (US)

( * ) Notice: Subject to any disclaimer, the term of this patent is extended or adjusted under 35 U.S.C. 154(b) by 356 days.

(21) Appl. No.: 12/839,968

(22) Filed: Jul. 20, 2010

(65) Prior Publication Data
US 2012/0021402 A1    Jan. 26, 2012

(51) Int. Cl.
*H01L 29/66* (2006.01)
*H01L 21/335* (2006.01)

(52) U.S. Cl. ............. 257/253; 257/E29.166; 257/E21.4; 435/5; 438/49

(58) Field of Classification Search .................. 257/253, 257/296, E21.4, E29.166; 435/5, 38, 39, 435/40; 438/49; 506/39
See application file for complete search history.

(56) References Cited

U.S. PATENT DOCUMENTS

| | | | |
|---|---|---|---|
| 4,437,969 A | 3/1984 | Covington et al. | |
| 4,778,769 A | 10/1988 | Forrest et al. | |
| 5,719,033 A | 2/1998 | Ackley et al. | |
| 5,827,482 A * | 10/1998 | Shieh et al. | 422/82.02 |
| 7,053,439 B2 | 5/2006 | Kan et al. | |
| 2002/0093052 A1 | 7/2002 | Masuda | |
| 2003/0071320 A1 | 4/2003 | Kocon | |
| 2006/0016699 A1 | 1/2006 | Kamahori | |
| 2010/0050745 A1 | 3/2010 | Liu | |

FOREIGN PATENT DOCUMENTS

EP    0065350 A1    11/1982

OTHER PUBLICATIONS

International Search Report for International Patent Application No. PCT/US2011/044166 (Mar. 20, 2012).

* cited by examiner

*Primary Examiner* — Julio J Maldonado
*Assistant Examiner* — Daniel Shook
(74) *Attorney, Agent, or Firm* — LeClairRyan, a Professional Corporation (57) ABSTRACT

A biosensor has one or more field effect transistors each comprising a source region and a drain region separated by a channel region and a gate positioned offset and spaced from the channel region. The biosensor also has one or more molecular probes coupled to at least one of the channel region and the offset gate, the one or more molecular probes configured to mate with at least one target. A method for detection of a target is also disclosed. One or more targets are immobilized as an electric field shunt between an offset gate and a channel region for one or more biosensors. A target measurement value is determined in proportion to a number of the one or more biosensors having the electric field shunt.

40 Claims, 7 Drawing Sheets

BIOSENSOR APPARATUSES AND METHODS THEREOF

FIELD

This technology generally relates to biosensors, and more specifically to biosensors having a field effect transistor gate positioned offset from a channel region to utilize a target mated with one or more molecular probes coupled to the gate and/or channel region as an electric field shunt between the offset gate and the channel region.

BACKGROUND

Sensors, and especially sensors capable of sensing biological targets, are in great demand for applications such as the detection of disease causing pathogens in water. Many types of the sensors proposed for biological detection utilize technologies such as microfluidics, polymerase chain reaction (PCR) target amplification, piezoelectric materials, or ion sensitive field effect transistors (ISFETs). Unfortunately, many of these techniques require filtration and culturing of biological samples, and are therefore unsuitable for real-time monitoring of fluid conditions. For example, ISFET sensors, functionalized with molecular probes, rely on an increase of charge near the surface of an FET channel region in order to indicate the presence of a target. These systems typically have large gate areas, thereby requiring high concentrations of multiple immobilized targets for a given device in order to obtain a meaningful positive test result. Accordingly, test results may take a long time to obtain while test samples are cultured, real-time results are not practical, and measurement resolution is sacrificed as original concentrations may be unknown.

SUMMARY

A biosensor has one or more field effect transistors each comprising a source region and a drain region separated by a channel region and a gate positioned offset and spaced from the channel region. The biosensor also has one or more molecular probes coupled to at least one of the channel region and the offset gate, the one or more molecular probes configured to mate with at least one target.

A method for detection of a target includes immobilizing one or more targets as an electric field shunt between an offset gate and a channel region for one or more biosensors. A target measurement value is determined in proportion to a number of the one or more biosensors having the electric field shunt.

A method for making a biosensor apparatus includes forming one or more field effect transistors. Each of the field effect transistors comprises a source region and a drain region separated by a channel region and a gate positioned offset and spaced from the channel region. One or more molecular probes are coupled to at least one of the channel region and the offset gate, the one or more molecular probes configured to mate with at least one target.

A computer readable medium having stored thereon instructions for detection of a target is disclosed. The instructions comprise machine executable code which when executed by at least one processor, causes the processor to perform steps including determining a target measurement value in proportion to a number of one or more biosensors having an electric field shunt. The electric field shunt is caused by the target being immobilized between an offset gate and a channel region for the one or more biosensors.

A biosensing system has a biosensor array and a controller. The biosensor array has one or more field effect transistors comprising a source region and a drain region separated by a channel region and a gate positioned offset and spaced from the channel region. The biosensor array also has one or more molecular probes coupled to at least one of the channel region and the offset gate, the one or more molecular probes configured to mate with at least one target. The controller is coupled to the biosensor array and configured to determine a target measurement value in proportion to a number of the one or more field effect transistors having an electric field shunt caused by the target immobilized between the offset gate and the channel region.

This technology provides a number of advantages including providing more effective and efficient biosensor apparatuses. The technology disclosed herein does not rely on the ionic potential of a target as a whole, but rather examples of the technology utilize the target's strong dipole moment (high relative permittivity) as an electric field shunt between an offset gate and a channel region of a field effect transistor. Therefore, the disclosed biosensor apparatuses may have very small dimensions allowing a single target microbe to be detected and monitored in real time. Furthermore, the disclosed biosensor apparatuses do not require analyte preparation (for example, no lysing of cells, no reagents, no debris filtering, no PCR for target amplification), and are compatible with existing integrated circuit manufacturing techniques.

It will be appreciated that for purposes of clarity and where deemed appropriate, reference numerals have been repeated in the figures to indicate corresponding features. Illustrations are not necessarily drawn to scale. While a biosensor apparatus and method for detection of a target are described herein by way of example for several embodiments and illustrative drawings, those skilled in the art will recognize that the system and method are not limited to the embodiments or drawings described. It should be understood, that the drawings and detailed description thereto are not intended to limit embodiments to the particular form disclosed. Rather, the intention is to cover all modifications, equivalents and alternatives falling within the spirit and scope of the appended claims. Any headings used herein are for organizational purposes only and are not meant to limit the scope of the description or the claims. As used herein, the word "may" is used in a permissive sense (i.e., meaning having the potential to), rather than the mandatory sense (i.e., meaning must). Similarly, the words "include", "including", and "includes" mean including, but not limited to.

DETAILED DESCRIPTION

Figure 1A:
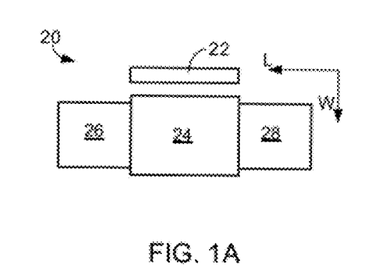
FIG. 1A is a top view of an exemplary field effect transistor having a gate positioned offset and spaced from a channel region.
Figure 1B:
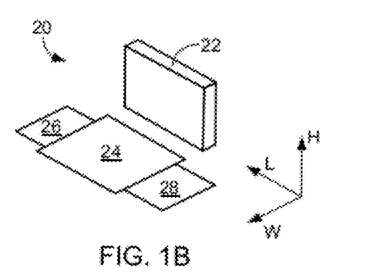
FIG. 1B is a perspective view of the exemplary field effect transistor of FIG. 1A.

FIG. 1A is a top view of an exemplary field effect transistor (FET) 20 having a gate 22 positioned offset and spaced from a channel region 24. FIG. 1B is a perspective view of the exemplary FET 20 of FIG. 1A. The FET 20 has a source region 26 and a drain region 28 which are separated by the channel region 24. In some embodiments, the source region 26, the drain region 28, and the channel region 24 are formed in a substrate (not shown). Non-limiting examples of FET 20 substrates may include silicon and gallium arsenide. The source region 26 and the drain region 28 may include a first type of semiconductor, while the channel region 24 may include a second type of semiconductor. Suitable types of semiconductors for forming a source region 26, a drain region 28, and a channel region 24 are known to those skilled in the art and may easily be selected, depending on the embodiment.

The channel region 24 has a channel length along a length (L) axis and a channel width along a width (W) axis. In the embodiment of FIGS. 1A and 1B, the gate 22 is spaced from the channel region 24 in a direction parallel to the W-axis. The gate 22 is also orthogonally offset from the channel region 24 in a direction parallel to a height (H) axis. In this embodiment, the gate 22 has a gate height parallel to the H-axis and a gate length parallel to the L-axis. In other embodiments, the gate 22 may have other locations and/or there may even be multiple offset gates for the FET. In this embodiment, the length of gate 22 is substantially parallel to a length of the channel region 24. As illustrated in FIG. 1, none of the surfaces of the offset gate FET (OGFET) 20 have been functionalized to mate with a target substance. Therefore, in this configuration, the OGFET 20 can act as a reference FET. The OGFET 20 is one of the building blocks of a biosensor as discussed below.

Figure 2:
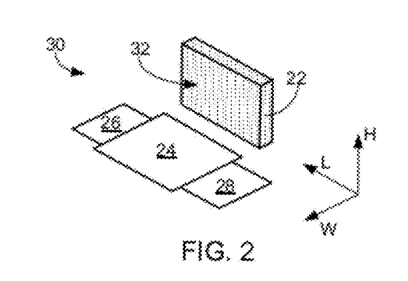
FIG. 2 is a perspective view of an exemplary biosensor having one or more molecular probes coupled to an offset gate of a field effect transistor.
Figure 3:
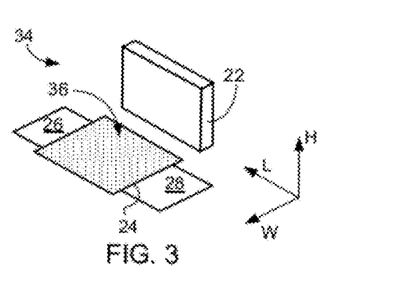
FIG. 3 is a perspective view of an exemplary biosensor having one or more molecular probes coupled to a channel region of a field effect transistor.

FIG. 2 is a perspective view of an exemplary biosensor 30 having one or more molecular probes 32 (shown with stippling) coupled to an offset gate 22 of a field effect transistor having a source region 26 and a drain region 28 separated by a channel region 24, similar to the OGFET embodiments discussed above. Alternatively, in some embodiments, as shown in the perspective view of FIG. 3, a biosensor 34 may have one or more molecular probes 36 (shown with stippling) coupled to the channel region 24. The channel region 24 will typically be covered by a channel insulator (not shown for ease of explanation), such as, but not limited to silicon dioxide, and the one or more molecular probes 36 may be coupled to the channel region 24 indirectly by coupling first to the channel insulator. In further embodiments, as shown in the perspective view of FIG. 4, a biosensor 38 may have one or more molecular probes 40 (shown with stippling) coupled to both the offset gate 22 and the channel region 24.

Figure 5:
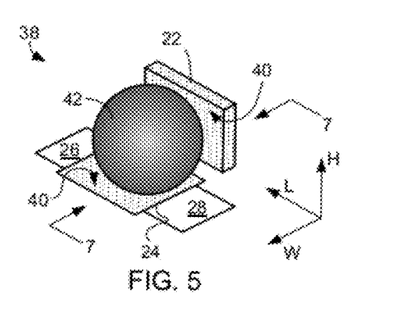
FIG. 5 is a perspective view of the biosensor illustrated in FIG. 4 mated with an immobilized target.

As shown in the perspective view of FIG. 5, the one or more molecular probes 40 are configured to mate with at least one target 42. Non-limiting examples of a suitable target 42 include a microbial pathogen, a bacteria, a virus, a toxin, a parasite, a molecule, *Cryptosporidium parvum* protozoa, *Cryptosporidium hominis*, *Eschericia coli*, *Vibrio cholerae* bacteria, *Clostridium botulinum* bacteria, *Salmonella typhi* bacteria, *Salmonella*, Hepatitis A virus, *Shigella dysenteriae* bacteria, *Entamoeba histolytica* amoeba, poliovirus, *Giardia lamblia* protozoa, *Entamoeba histolytica*, *Cyclospora cayetanensis*, *Microsporidia*, *Schistosoma*, *Dracunculus medinensis*, *Clostridium botulinum*, *Campylobacter jejuni*, *Vibrio cholerae*, *Mycobacterium marinum*, *Legionella pneumophila*, and *Leptospira* bacteria. Suitable molecular probes 40 are known to those skilled in the art and can be used to functionalize the offset gate 22 and/or the channel region 24 for a particular target, depending on the embodiment.

Figure 4:
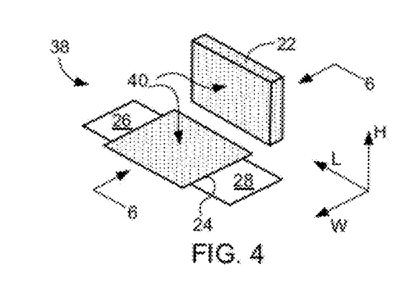
FIG. 4 is a perspective view of an exemplary biosensor having one or more molecular probes coupled to an offset gate and a channel region of a field effect transistor.
Figure 6:
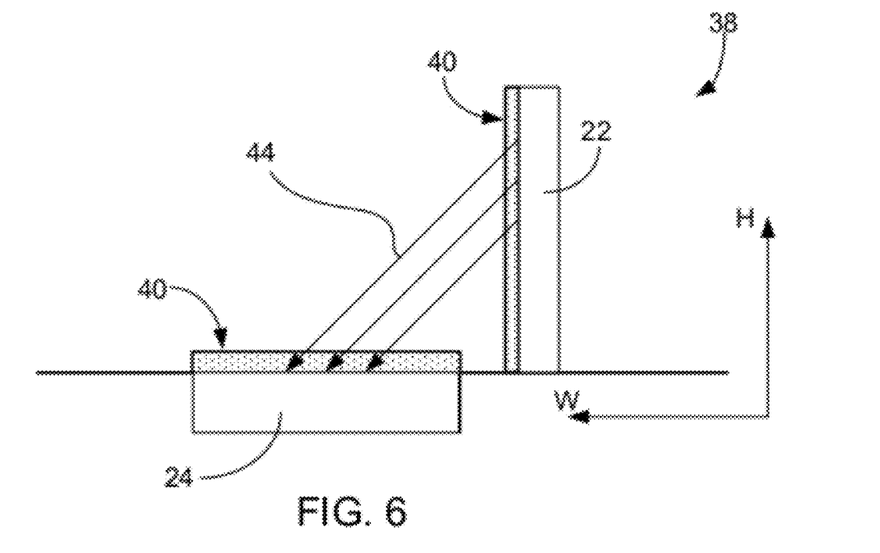
FIG. 6 is a side cross-sectional view of the biosensor shown in FIG. 4 illustrating a weak electric field between the offset gate and the channel region in the absence of an immobilized target.

FIG. 6 is a side cross-sectional view of the biosensor 38 shown in FIG. 4 illustrating a weak electric field 44 between the offset gate 22 and the channel region 24 in the absence of an immobilized target. The offset gate 22 is configured to receive a gate bias voltage. The offset gate 22 is spaced and positioned offset from the channel region 24 such that the gate bias voltage creates the weak electric field 44 in the absence of an immobilized target. The weak electric field 44 is not strong enough to create an inversion layer in the channel region 24, thereby substantially preventing anything other than leakage current from passing between the source region and the drain region. In this condition, the biosensor 38 will appear to be in an off state, indicating that there is no target present.

Figure 7:
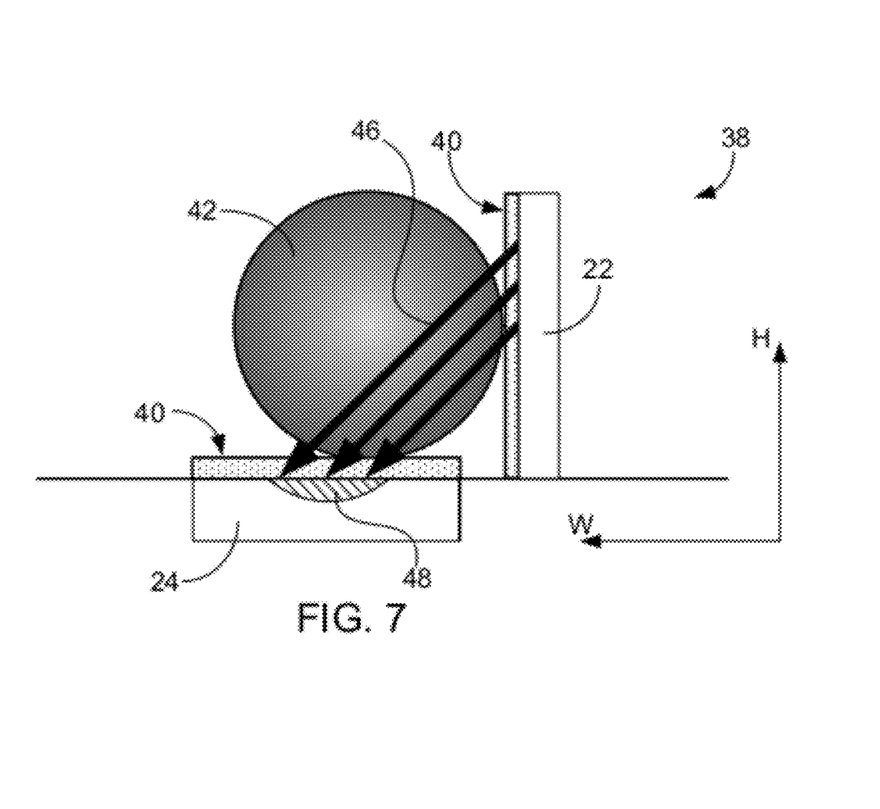
FIG. 7 is a side cross-sectional view of the biosensor shown in FIG. 5 illustrating a stronger electric field between the offset gate and the channel region when a target is immobilized between the offset gate and the channel region.

FIG. 7 is a side cross-sectional view of the biosensor 38 shown in FIG. 5 illustrating a stronger electric field 46 between the offset gate 22 and the channel region 24 when a target 42 is immobilized between the offset gate 22 and the channel region 24. For a given gate bias voltage or range of gate bias voltages, the channel region 24 and gate 22 are positioned with respect to each other based on a footprint of the target 42 to utilize the target 42 mated with the one or more molecular probes 40 as an electric field shunt between the offset gate 22 and the channel region 24. Target substances, such as microbial pathogens, typically have a very strong dipole moment causing a very high relative permittivity. For example, the relative permittivity of *Escherichia coli* at low frequencies is approximately 800,000. Therefore, after the immobilization of the target 42, the region between the offset gate 22 and the channel region 24 is effectively filled with an extremely high relative permittivity material. In this case the electric field 46 from an appropriate bias on the offset gate 22 is sufficient to form a channel inversion layer 48 between the source region and the drain region, thereby indicating the presence of an immobilized target pathogen. In this condition, current can flow between the source region 26 and the drain region 28, and the biosensor 38 will appear to be in an on state, indicating that there is a target 42 present.

As mentioned above, a given one or more molecular probes 40 coupled to the channel region and/or the offset gate may be chosen to mate with one or more target. Some embodiments may be configured to immobilize a single target. In such configurations, it may be desirable to size the channel length and width to match a footprint of the target. Alternatively, or additionally, it may desirable in certain embodiments to size the gate height and length to match a footprint of the target. With such sizings, once a single target is immobilized by the one or more molecular probes coupled to the gate and/or the channel region, the sensor can detect the single instance of the target while the target remains bonded to (mated with) the one or more molecular probes. Furthermore, the one or more molecular probes may be chosen by those skilled in the art to have a target binding energy suitable to enable an electrical interrogation of the channel region before a bond between one or more molecular probes and the target is broken.

Figure 8A:
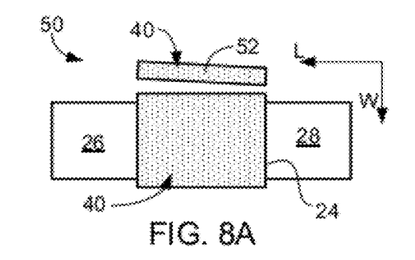
FIG. 8A is a top view of an exemplary biosensor having an offset gate which is not spaced parallel from a channel region.
Figure 8B:
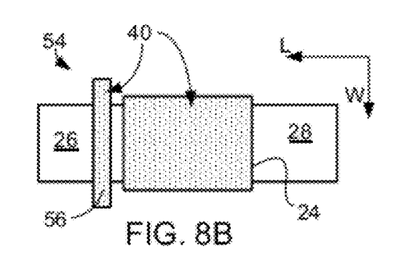
FIG. 8B is a top view of an exemplary biosensor having an offset gate which is over a source region.
Figure 8C:
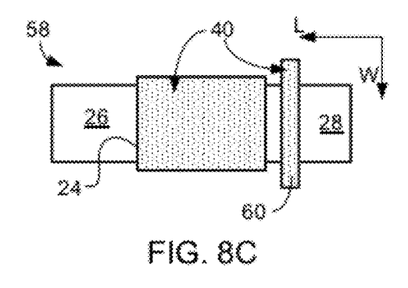
FIG. 8C is a top view of an exemplary biosensor having an offset gate which is over a drain region.
Figure 8D:
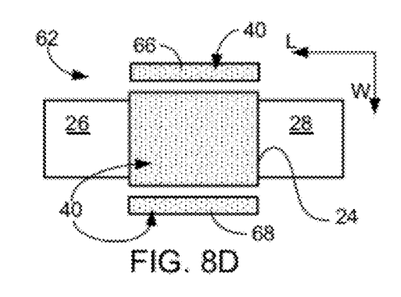
FIGS. 8D and 8E are top views of exemplary biosensors having multiple offset gates which are positioned offset and spaced from a channel region.
Figure 8E:
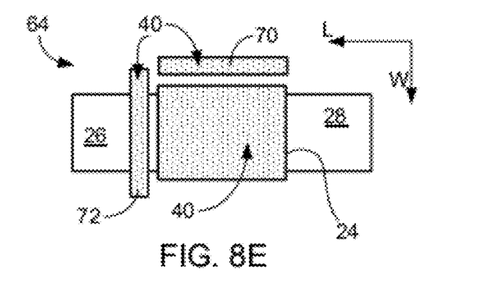

Depending on the embodiment, the offset gate may exist in one or more of a variety of configurations in addition to those already discussed. For example, FIG. 8A is a top view of an exemplary biosensor 50 having an offset gate 52 which is not spaced parallel from a channel region 24. FIG. 8B is a top view of an exemplary biosensor 54 having an offset gate 56 which is over a source region 26. In such an embodiment, the gate 56 would need to be electrically insulated from the source region 26. Such insulation could take the form of silicon dioxide, among other suitable insulator choices known to those skilled in the art. FIG. 8C is a top view of an exemplary biosensor 58 having an offset gate 60 which is over a drain region 28. Again, in such an embodiment, the gate 60 would need to be electrically insulated from the drain region 28. FIGS. 8D and 8E are top views of an exemplary biosensors 62 and 64 having multiple offset gates 66, 68 and 70, 72 respectively, which are positioned offset and spaced from the channel region 24. As in previously discussed embodiments, although the channel region and offset gates of FIGS. 8A-8E were all illustrated as being functionalized with one or more molecular probes 40, only one or more of the channel region and/or one of the gates needs to be coupled to the one or more molecular probes.

Figure 9:
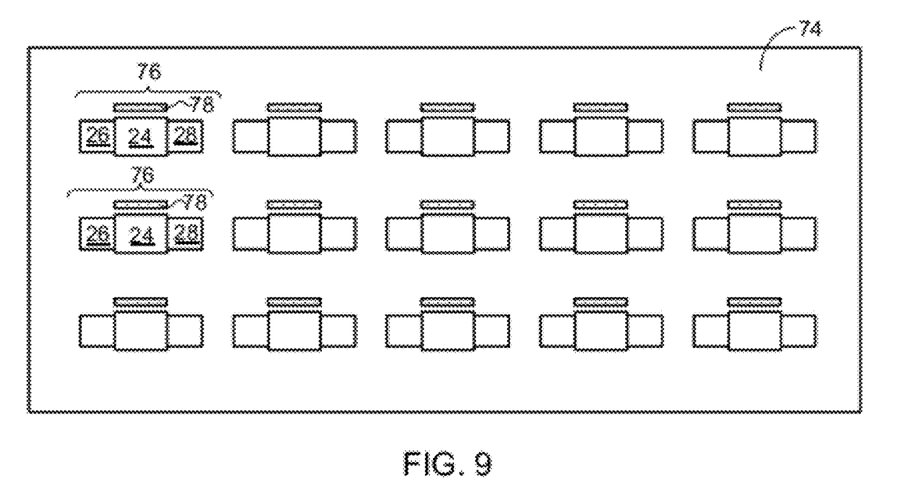
FIG. 9 is an exemplary biosensor array.

The embodiments of biosensors described above, and their equivalents, may be fabricated using existing integrated circuit and micro-electro-mechanical-system (MEMS) fabrication techniques. Therefore, one or more bio sensors may be built in batches on a single array and/or built as part of an integrated circuit. FIG. 9 is an exemplary biosensor array 74. The array 74 has multiple OGFETs 76, the features of which have been described above. In this example, the OGFETs 76 each have their own functionalized offset gate 78. Depending on the embodiment, the offset gates 78 may all be functionalized to mate with the same type of target. In other embodiments, different groups of offset gates may be functionalized to mate with different types of a target. Circuit traces for accessing the source region 26, drain region 28, and gate 78 for each FET biosensor may be included with the sensor array 74, but are not shown for simplicity. Those skilled in the art can easily fabricate circuit traces and/or addressing circuitry to provide access to and/or address the individual sensors 78.

Figure 10:
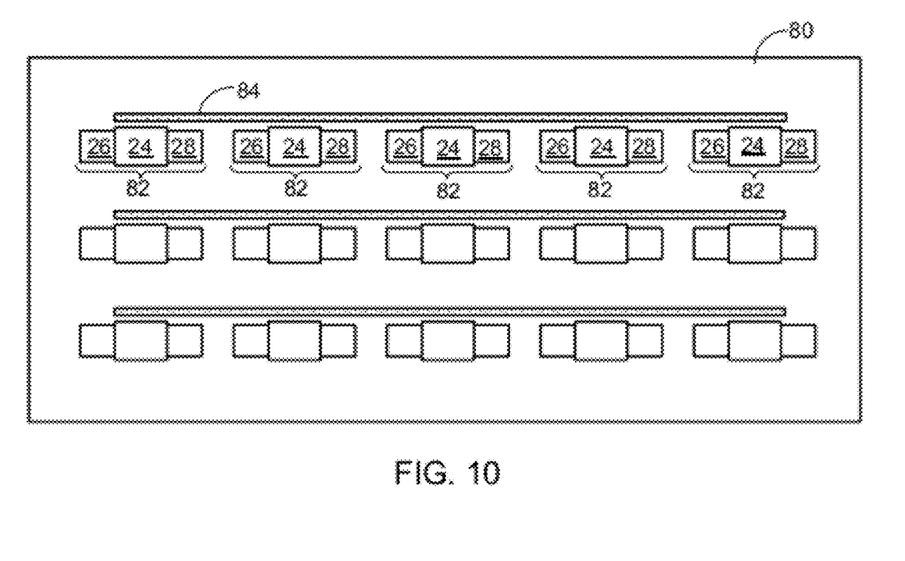
FIG. 10 is an exemplary biosensor array where multiple biosensors share a common offset gate.

FIG. 10 is another exemplary biosensor array 80 where multiple biosensors 82 share a common offset gate 84. The use of shared gates 84 may simplify the number of circuit traces needed in an array 80.

Figure 11:
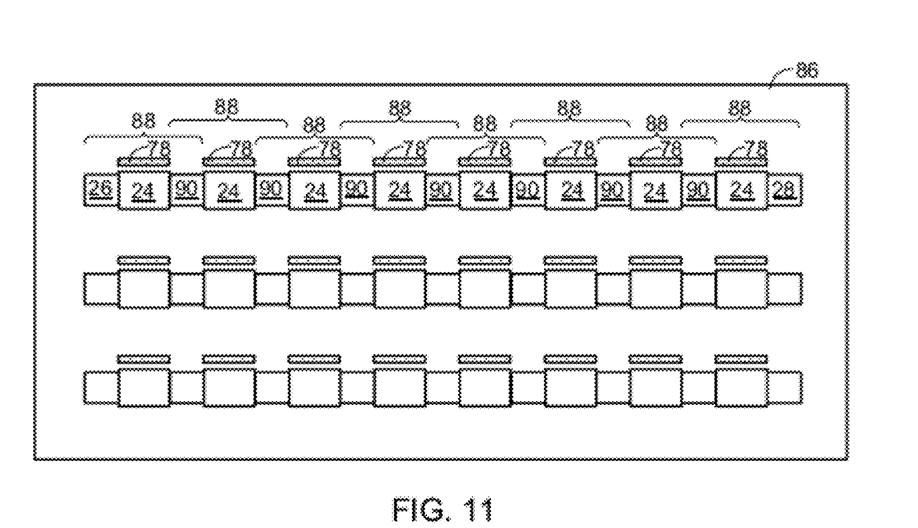
FIG. 11 is an exemplary biosensor array having shared drain and source regions.

FIG. 11 is a further exemplary biosensor array 86. The array 86 has multiple OGFETs 88 having shared drain and source regions 90. Each OGFET sensor 88 can be addressed and read independently of its neighbor, and the shared drain and source regions 90 enable more compact spacing of sensors and may reduce the total number of circuit traces needed for the array 86.

Figure 12:
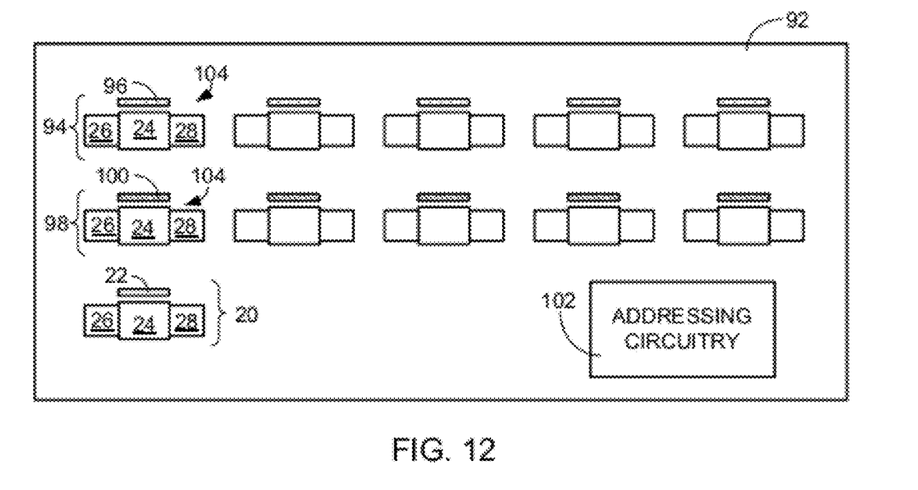
FIG. 12 is an exemplary biosensor array having a first group of biosensors having offset gates configured to mate with a first target, a second group of biosensors having offset gates configured to mate with a second target, a reference field effect transistor, and addressing circuitry.

FIG. 12 is another exemplary biosensor array 92. The array 92 has a first group of OGFET biosensors 94 having offset gates 96 configured to mate with a first target, and a second group of biosensors 98 having offset gates 100 configured to mate with a second target. This embodiment also has at least one reference field effect transistor 20 which has no functionalized surfaces. The reference FET 20 may be monitored to determine a reference reading which can be subtracted from the functionalized sensor readings to remove unwanted background noise from biosensor measurements. The array 92 in this embodiment also has addressing circuitry 102 to provide a more simplified interface between the array 92 and a processing device which might be coupled to the array 92. Types of addressing circuitry are well known to those skilled in the art, and may include, for example, one or more input decoders, one or more output decoders, and/or data buffers for querying and reading individual sensors 104. Other embodiments of biosensor arrays may simply provide circuit traces for each sensor element and leave it to one or more external devices to deal with addressing.

Figure 13:
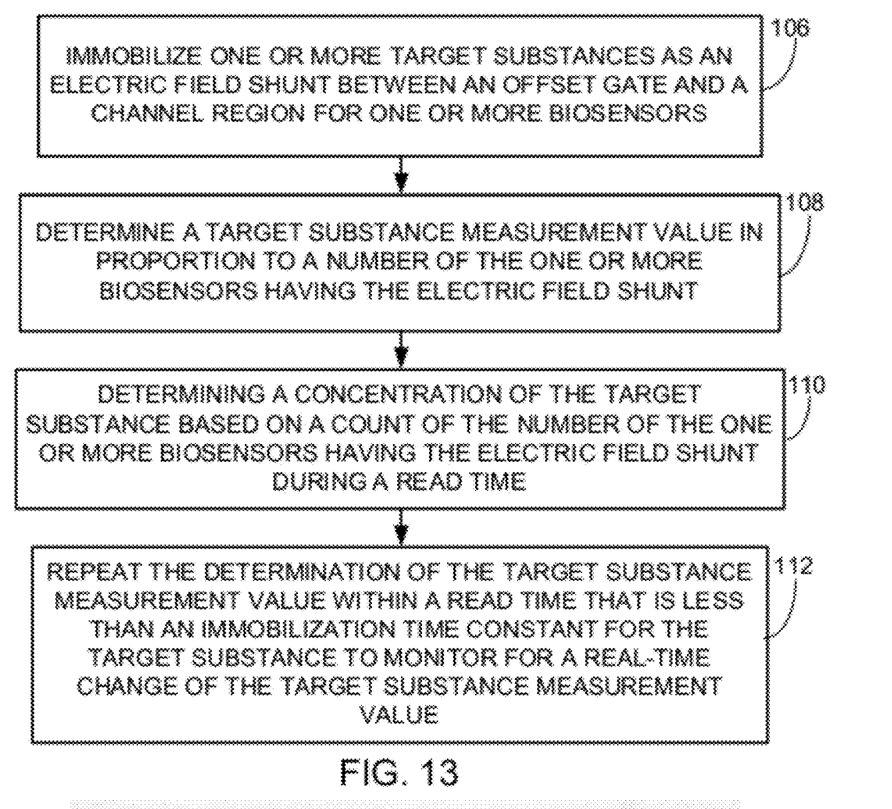
FIG. 13 is a flow chart of an exemplary method for detection of a target.

FIG. 13 is a flow chart of an exemplary method for detection of a target. In step 106, one or more target substances are immobilized as an electric field shunt between an offset gate and a channel region for one or more biosensors. The one or more molecular probes coupled to the channel region and/or the offset gate of the OGFET biosensor embodiments discussed above, and their equivalents, provide a suitable structure for accomplishing this action. As also discussed, the immobilization does not necessarily need to be permanent or long lasting. Instead, the one or more molecular probes may have a target binding energy suitable to enable an electrical interrogation of the channel region, for example in the following steps, before a bond between the one or more molecular probes and the target is broken.

In step 108, a target substance measurement value is determined in proportion to a number of the one or more biosensors having the electric field shunt. In some embodiments, this may be done by monitoring each of the one or more biosensors during a read time to count the number of the one or more biosensors having the electric field shunt. As discussed above, current will flow between the source region and the drain region if a gate bias voltage is applied to the offset gate while a target is mated with the one or more molecular probes on the offset gate and/or the channel region. As each sensor is interrogated, flow of current or a reading of a corresponding voltage from the current flow can be counted for each sensor.

Figure 14:
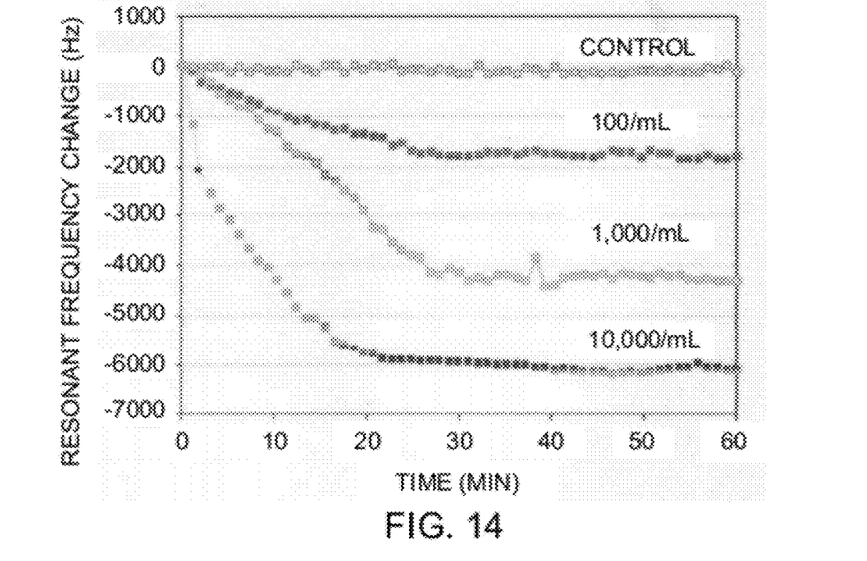
FIG. 14 is a graph of resonant frequency as a function of time for a piezoelectric cantilever functionalized to mate with a target biological species.

In some embodiments, as shown in step 110, a concentration of the target may be determined based on the count of the number of the one or more biosensors having the electric field shunt for the read time. For example, FIG. 14 is a graph showing resonant frequency as a function of time for a piezoelectric cantilever (a different type of functionalized sensor) functionalized to mate with a target biological species. In the related experiment, in a flow configuration at 1 mL/min, the resonant frequency of the functionalized piezoelectric cantilever was observed to be concentration dependent for a pathogen. A measure of a decrease in resonant frequency was the indication of immobilization of the target pathogen. Three different concentrations (100, 1,000, and 10,000 per ml) of oocysts were studied. Observation of the plots in FIG. 14 shows resonant frequency shift saturation for each concentration was reached at approximately the same time interval (an immobilization time constant) and, more importantly, the resonant frequency shift is concentration dependent. Without wishing to be tied to a particular theory, this is most likely due to a finite average immobilization retention time. This observation has lead to the discovery that molecular probes may be tailored with a target binding energy. As discussed above, in some embodiments, the binding energy may be chosen so the target will remain immobilized for an average retention time sufficient for electrical interrogation and thus detection. However, beyond the average immobilization retention time the target/probe bond will break thus creating a self-regenerating detection array. A self-regenerating bio-sensor array has significant advantages for cost and reduced maintenance. This is especially important in third world locations where replacement bio-sensor arrays would not be readily available. In some embodiments, the read time could be less than an immobilization time constant for the target in order to facilitate real-time readings which are more sensitive to fluctuations in concentrations. For example, in step 112, the determination of the target substance measurement value could be repeated within a read time that is less than an immobilization time constant for the target substance to monitor for a real-time change of the target substance measurement value. In other embodiments, the read time might be longer than the immobilization time constant to ensure that a steady state reading is achieved.

In some embodiments, rather than keeping a count of sensor cells, the target measurement value may be determined in proportion to the number of the one or more biosensors having the electric field shunt by measuring a total current for the one or more biosensors.

Figure 15:
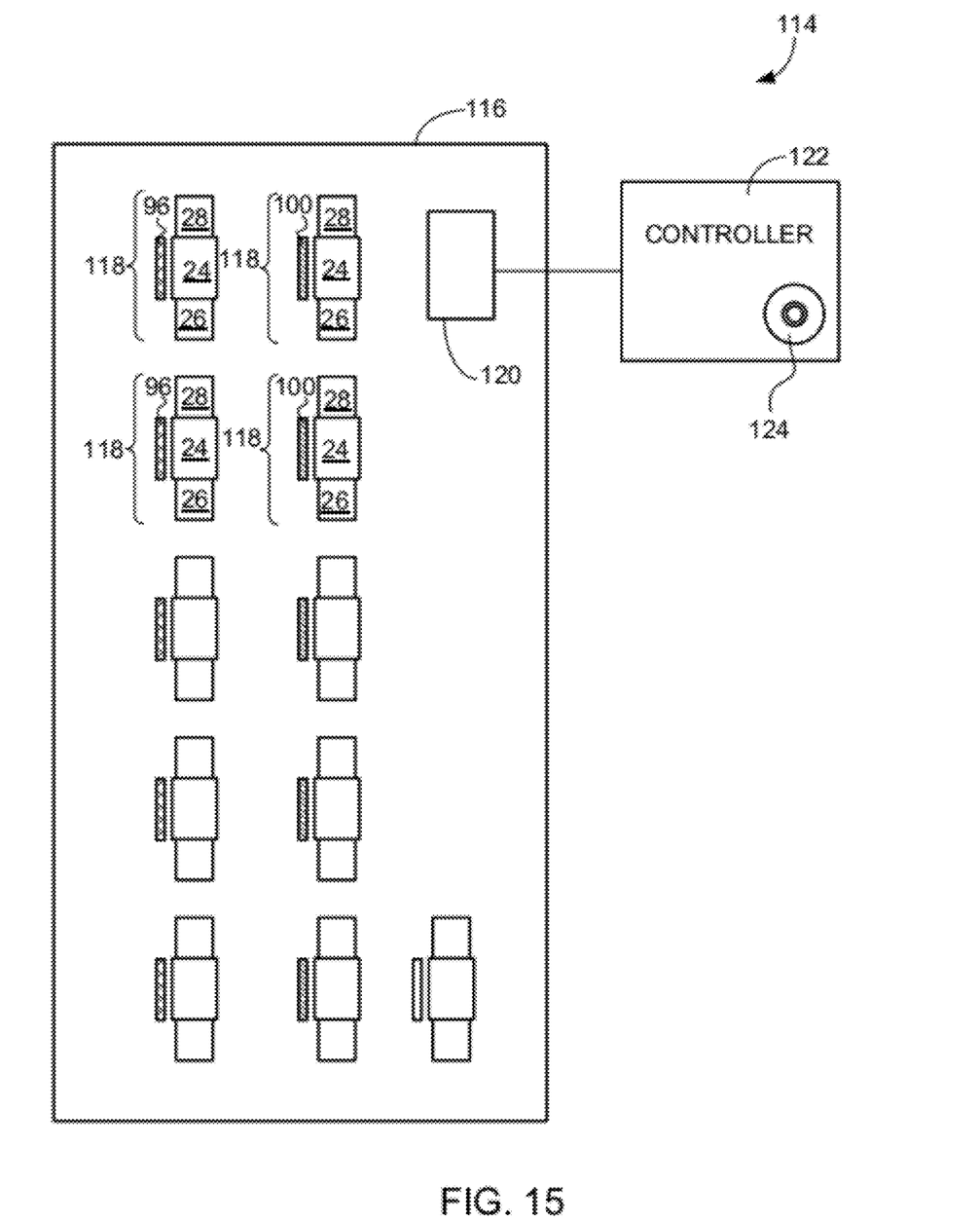
FIG. 15 is an exemplary biosensing system.

FIG. 15 is an exemplary biosensing system 114. The system 114 has a biosensor array 116 having one or more field effect transistors 118, each of the field effect transistors 118 comprising a source region 26 and a drain region 28 separated by a channel region 24 and a gate 22 positioned offset and spaced from the channel region 24 such as discussed in the embodiments above. As also previously discussed, one or more molecular probes are coupled to at least one of the channel region 24 and the offset gate 22, the one or more molecular probes being configured to mate with at least one target. In this embodiment, the biosensor array 116 also has addressing circuitry 120 to provide access to one or more OGFETs 118. The system 114 also has a controller 122 coupled to the biosensor array 116 and configured to determine a target measurement value in proportion to a number of the one or more biosensors 118 having an electric field shunt caused by the target immobilized between the offset gate and the channel region for the one or more field effect transistors. Suitable methods for the determination of the target measurement value have been discussed above.

The controller 122 is coupled for communication with the addressing circuitry 120, although the controller 122 can be coupled to other numbers and types of systems, devices, components, and other elements in other configurations. In this example, the controller 122 is a computing device with at least one central processing unit (CPU) or processor, at least one memory, and an interface unit which are coupled together by a bus or other numbers and types of links, although the controller 122 could comprise other numbers and types of systems, devices, components and other elements in other configurations.

The central processing unit (CPU) or processor of the controller 122 executes a program of stored instructions for one or more aspects of the technology as described herein. The memory of the controller 122 stores these programmed instructions for one or more aspects of the technology as described herein, although some or all of the programmed instructions could be stored and/or executed elsewhere. A variety of different types of memory storage devices, such as a random access memory (RAM) or a read only memory (ROM) in the system or a floppy disk, hard disk, CD ROM, DVD ROM, or other computer readable medium which is read from and/or written to by a magnetic, optical, or other reading and/or writing system that is coupled to the processor of the controller 122, can be used for the memory of the controller 122. The interface unit of the controller 122 is used to operatively couple communications between the controller 122 and the addressing circuitry 120, although other types and numbers of systems, devices, components, and other elements could be coupled together for communications.

Although an exemplary controller 122 is described and illustrated herein, other types and numbers of systems, devices, components, and other elements in other configurations could be used. It is to be understood that the controller 122 described herein is for exemplary purposes, as many variations of the specific hardware and software used to implement the examples are possible, as will be appreciated by those skilled in the relevant art(s).

Furthermore, the controller 122 may be conveniently implemented using one or more general purpose computer systems, microprocessors, application specific integrated circuits, field programmable gate arrays, digital signal processors, and micro-controllers, programmed according to the teachings of the examples, as described and illustrated herein, and as will be appreciated by those ordinary skill in the art.

In addition, two or more computing systems or devices can be substituted for the controller 122 in any example. Accordingly, principles and advantages of distributed processing, such as redundancy and replication also can be implemented, as desired, to increase the robustness and performance of the devices and systems of the examples. The examples may also be implemented on computer system or systems that extend across any suitable network using any suitable interface mechanisms and communications technologies, including by way of example only telecommunications in any suitable form (e.g., voice and modem), wireless communications media, wireless communications networks, cellular communications networks, G3 communications networks, Public Switched Telephone Network (PSTNs), Packet Data Networks (PDNs), the Internet, intranets, and combinations thereof.

The examples of the operation of the controller 122 may also be embodied as a computer readable medium 124 having instructions stored thereon for one or more aspects of the technology as described and illustrated by way of the examples herein, which when executed by a processor, cause the processor to carry out the steps necessary to implement the methods of the examples, as described and illustrated herein.

Having thus described the basic concept of the invention, it will be rather apparent to those skilled in the art that the foregoing detailed disclosure is intended to be presented by way of example only, and is not limiting. Various alterations, improvements, and modifications will occur and are intended to those skilled in the art, though not expressly stated herein. These alterations, improvements, and modifications are intended to be suggested hereby, and are within the spirit and scope of the invention. Additionally, the recited order of processing elements or sequences, or the use of numbers, letters, or other designations therefor, is not intended to limit the claimed processes to any order except as may be specified in the claims. Accordingly, the invention is limited only by the following claims and equivalents thereto.

What is claimed is:

1. A bio sensor apparatus comprising:
   one or more field effect transistors, each of the field effect transistors comprising a source region and a drain region separated by a channel region and a gate positioned offset and spaced from the channel region; and
   one or more molecular probes coupled to at least one of the channel region and the offset gate, the one or more molecular probes configured to mate with at least one target.

2. The biosensor of claim 1, wherein the source region and the drain region each comprise a first type of semiconductor and the channel region comprises a second type of semiconductor.

3. The biosensor of claim 1, wherein each of the field effect transistors further comprises a substrate in which the source region, the drain region, and the channel region are formed.

4. The biosensor of claim 1, wherein the channel region has a channel length and a channel width which are approximately sized to match a footprint of the target.

5. The biosensor of claim 1, wherein the gate has a gate height and a gate length which are approximately sized to match a footprint of the target.

6. The biosensor of claim 1, wherein the gate has a length which is substantially parallel to a length of the channel region.

7. The biosensor of claim 1, wherein the gate is over the source region.

8. The biosensor of claim 1, wherein the gate is over the drain region.

9. The biosensor of claim 1, further comprising at least one additional offset gate.

10. The biosensor of claim 1, wherein the target is selected from the group consisting of a microbial pathogen, a bacteria, a virus, a toxin, a parasite, a molecule, *Cryptosporidium parvum* protozoa, *Cryptosporidium hominis*, *Eschericia coli*, *Vibrio cholerae* bacteria, *Clostridium botulinum* bacteria, *Salmonella typhi* bacteria, *Salmonella*, Hepatitis A virus, *Shigella dysenteriae* bacteria, *Entamoeba histolytica* amoeba, poliovirus, *Giardia lamblia* protozoa, *Entamoeba histolytica*, *Cyclospora cayetanensis*, *Microsporidia*, *Schistosoma*, *Dracunculus medinensis*, *Clostridium botulinum*, *Campylobacter jejuni*, *Vibrio cholerae*, *Mycobacterium marinum*, *Legionella pneumophila*, and *Leptospira* bacteria.

11. The biosensor of claim 1, wherein the channel region and gate are positioned with respect to each other based on a footprint of the target to utilize the target mated with the one or more molecular probes as an electric field shunt between the offset gate and the channel region.

12. The biosensor of claim 1, wherein the offset gate is configured to receive a gate bias voltage and is spaced and positioned offset from the channel region such that:
   an inversion layer is not created in the channel region in the absence of a target being immobilized by the one or more molecular probes while the gate bias voltage is applied to the offset gate; and
   the inversion layer is created in the channel region when the target is immobilized by the one or more molecular probes while the gate bias voltage is applied to the offset gate.

13. The biosensor of claim 1, wherein the one or more molecular probes have a target binding energy suitable to enable an electrical interrogation of the channel region before a bond between the one or more molecular probes and the target is broken.

14. The biosensor of claim 1, wherein the source region of at least one of the one or more field effect transistors comprises the drain region of another of the one or more field effect transistors.

15. The biosensor of claim 1, wherein the gates of at least two of the one or more field effect transistors comprise a shared gate.

16. The biosensor of claim 1, wherein:
   the one or more field effect transistors comprise a first group of one or more field effect transistors and a second group of one or more field effect transistors;
   the one or more molecular probes coupled to at least one of the channel region and the offset gate for each of the first group of one or more field effect transistors are configured to mate with a first target; and
   the one or more molecular probes coupled to at least one of the channel region and the offset gate for each of the second group of one or more field effect transistors are configured to mate with a second target.

17. The biosensor of claim 1 further comprising one or more reference field effect transistors, each of the reference field effect transistors comprising a source region and a drain region separated by a channel region and a gate positioned offset from the channel region.

18. The biosensor of claim 1, further comprising circuitry configured to address the one or more field effect transistors.

19. A method for detection of a target, the method comprising:
   providing one or more biosensors with an offset gate and a channel region configured to mate with one or more targets and form an electric field shunt; and
   providing a controller that determines a target measurement value in proportion to a number of the one or more biosensors having the electric field shunt.

20. The method of claim 19, wherein the providing the controller further comprises providing the controller further configured to monitor each of the one or more biosensors during a read time to count the number of the one or more biosensors having the electric field shunt.

21. The method of claim 20 wherein the providing the controller further comprises providing the controller configured to determine a concentration of the target based on the count of the number of the one or more biosensors having the electric field shunt for the read time.

22. The method of claim 21, wherein the read time is less than an immobilization time constant for the target.

23. The method of claim 19, wherein the providing the controller further comprises providing the controller configured to repeat the determination of the target measurement value within a read time that is less than an immobilization time constant for the target to monitor for a real-time change of the target measurement value.

24. The method of claim 19, wherein the target measurement value comprises a total current for the one or more biosensors.

25. A method for making a biosensor apparatus, the method comprising:
   forming one or more field effect transistors, each of the field effect transistors comprising a source region and a drain region separated by a channel region and a gate positioned offset and spaced from the channel region; and coupling one or more molecular probes to at least one of the channel region and the offset gate, the one or more molecular probes configured to mate with at least one target.

26. The method of claim 25, wherein the channel region has a channel length and a channel width which are approximately sized to match a footprint of the target.

27. The method of claim 25, wherein the gate has a gate height and a gate length which are approximately sized to match a footprint of the target.

28. A non-transitory computer readable medium having stored thereon instructions for detection of a target comprising machine executable code which when executed by at least one processor, causes the processor to perform steps comprising:

identifying a number of one or more biosensors having an electric field shunt caused by a target immobilized between an offset gate and a channel region for the one or more bio sensors; and determining a target measurement value in proportion to the identified number of one or more biosensors having the electric field shunt caused by the target immobilized between the offset gate and the channel region.

29. The medium of claim 28, wherein the identifying the number of one or more biosensors having an electric field shunt caused by a target immobilized between an offset gate and a channel region for the one or more bio sensors further comprises monitoring each of the one or more biosensors during a read time to count the number of the one or more biosensors having the electric field shunt.

30. The medium of claim 29, further comprising determining a concentration of the target based on the count of the number of the one or more biosensors having the electric field shunt during the read time.

31. The medium of claim 29, wherein the read time is less than an immobilization time constant for the target.

32. The medium of claim 29, wherein the determining the target measurement value is based on a total measured current for the one or more biosensors.

33. The medium of claim 28, further comprising repeating the identifying and the determining within a read time that is less than an immobilization time constant for the target to monitor for a real-time change of the target measurement value.

34. A biosensing system, comprising:
a biosensor array comprising:
one or more field effect transistors, each of the field effect transistors comprising a source region and a drain region separated by a channel region and a gate positioned offset and spaced from the channel region; and
one or more molecular probes coupled to at least one of the channel region and the offset gate, the one or more molecular probes configured to mate with at least one target; and
a controller coupled to the biosensor array and configured to determine a target measurement value in proportion to a number of the one or more field effect transistors having an electric field shunt caused by the target immobilized between the offset gate and the channel region.

35. The system of claim 34, wherein the offset gate is configured to receive a gate bias voltage and is spaced from and positioned offset from the channel region such that:
an inversion layer is not created in the channel region in the absence of the target being immobilized by the one or more molecular probes while the gate bias voltage is applied to the offset gate; and
the inversion layer is created in the channel region when the target is immobilized by the one or more molecular probes while the gate bias voltage is applied to the offset gate.

36. The system of claim 34, wherein the one or more molecular probes have a target binding energy suitable to enable an electrical interrogation of the channel region before a bond between the one or more molecular probes and the target is broken.

37. The system of claim 34 wherein the biosensor array further comprises one or more reference field effect transistors, each of the reference field effect transistors comprising a source region and a drain region separated by a channel region and a gate positioned offset from the channel region.

38. The system of claim 34, further comprising circuitry configured to address the one or more field effect transistors.

39. The system of claim 34, wherein the controller is further configured to determine a concentration of the target based on a count of the number of the one or more field effect transistors having the electric field shunt for a read time.

40. The system of claim 39, wherein the read time is less than an immobilization time constant for the target.

* * * * *